(12) United States Patent
Doi et al.

(10) Patent No.: US 7,951,762 B2
(45) Date of Patent: May 31, 2011

(54) SKIN OR HAIR WASHING COMPOSITION

(75) Inventors: Yasuhiro Doi, Wakayama (JP); Masaki Inoue, Wakayama (JP)

(73) Assignee: Kao Corporation, Tokyo (JP)

( * ) Notice: Subject to any disclaimer, the term of this patent is extended or adjusted under 35 U.S.C. 154(b) by 360 days.

(21) Appl. No.: 12/159,105

(22) PCT Filed: Oct. 31, 2006

(86) PCT No.: PCT/JP2006/321783
§ 371 (c)(1),
(2), (4) Date: Jun. 25, 2008

(87) PCT Pub. No.: WO2007/077668
PCT Pub. Date: Jul. 12, 2007

(65) Prior Publication Data
US 2010/0222246 A1 Sep. 2, 2010

(30) Foreign Application Priority Data
Dec. 28, 2005 (JP) .................................. 2005-377501

(51) Int. Cl.
*C11D 1/72* (2006.01)
*C11D 1/835* (2006.01)
*C11D 1/86* (2006.01)
*C11D 1/92* (2006.01)
*C11D 3/37* (2006.01)

(52) U.S. Cl. ........ 510/119; 510/121; 510/123; 510/130; 510/505

(58) Field of Classification Search .................. 510/119, 510/121, 123, 130, 505
See application file for complete search history.

(56) References Cited

U.S. PATENT DOCUMENTS

| 5,942,478 A * | 8/1999 | Lopes ........................ 424/70.1 |
| 6,635,240 B1 * | 10/2003 | Bolich et al. ................ 424/70.1 |
| 6,923,954 B2 * | 8/2005 | Doi et al. .................... 424/70.19 |
| 2006/0248662 A1 * | 11/2006 | Legrand .......................... 8/405 |
| 2007/0128142 A1 * | 6/2007 | Harrison et al. ........... 424/70.12 |
| 2007/0238634 A1 * | 10/2007 | Foland et al. ................ 510/406 |

FOREIGN PATENT DOCUMENTS

| FR | 2862235 A | * 5/2005 |
| JP | 4 108723 | 4/1992 |
| JP | 7-53991 | 2/1995 |
| JP | 11-12594 | 1/1999 |
| JP | 2004 277685 | 10/2004 |
| JP | 2004-277685 A | * 10/2004 |
| WO | 97 14396 | 4/1997 |

* cited by examiner

*Primary Examiner* — Lorna M Douyon
(74) *Attorney, Agent, or Firm* — Oblon, Spivak, McClelland, Maier & Neustadt, L.L.P.

(57) ABSTRACT

A skin or hair washing composition having excellent foamability and a good feeling upon use in the process from washing to after drying, which comprises:
the following components (A), (B) and (C):
(A) a compound represented by formula (1):

$$R^1O\text{-}(AO)_n\text{-}R^2 \qquad (1)$$

(B) a surfactant other than the component (A); and
(C) a cationic polymer,
wherein the weight ratio of the component (A) and the component (C), (A)/(C), is from 0.5 to 60.

19 Claims, No Drawings

SKIN OR HAIR WASHING COMPOSITION

BACKGROUND OF THE INVENTION

1. Field of the Invention

The present invention relates to a skin or hair washing composition, such as hair shampoo or body shampoo, containing an adduct of an alkylene oxide having 2 to 4 carbon atoms linked to an alcohol having 8 to 10 carbon atoms (alkylene glycol ether), a surfactant and a specific cationic polymer.

2. Background of the Invention

Washing compositions are required to have various functions such as emulsifying power, solubilizing power or washing power against dirt components such as oil. Among them, a washing composition for the skin or the hair, as contrasted with any detergent composition for industrial use, is required to have good foaming properties and improved feeling upon use, such as good foamability and comfortable foam sensation during washing, and nice touch during rinsing or after drying (in the case of hair, finger-combability or softness of the hair, and in the case of the skin, ease of rinsing or the moist feeling after drying).

With the aim of improving the foaming properties or of adjusting the viscosity of washing compositions, a variety of foam enhancers and thickening agents have been developed so far, and fatty acid alkanolamides, fatty acid amidopropyl betaines or the like is typically used as a foam enhancer or thickening agent. However, these nitrogen-containing compounds tend to undergo color changes over time, depending on the mixing conditions thereof. Furthermore, fatty acid diethanolamide is suspected of causing carcinoma, when becoming a nitroso compound (i.e., one of the impurities thereof). For these reasons, there is an urgent need for developing a thickening/foam-enhancing agent containing no nitrogen.

Patent Document 1 describes a washing composition excellent in foamability as a thickening/foam-enhancing agent containing no nitrogen, obtained by employing an alcohol having 8 to 12 carbon atoms as a starting material, and comprising a combination of a (poly)ethylene glycol alkyl ether added with 1 to 3 moles of ethylene oxide, an anionic surfactant and/or a ampholytic surfactant.

Patent Documents 2 and 3 also disclose alkylene oxide adducts of higher aliphatic alcohols with short-chained ethylene oxide or propylene oxide introduced thereto, and these products are described to have improved foamability and improved low temperature stability. However, none of these documents make mention of the improvement of feeling upon use, and there is no mention about use of cationic polymers, either. These methods are also far from satisfactory in feeling upon use, especially in a feeling upon use required for a skin or hair washing composition.

Washing compositions for the skin or the hair are known to make use of cationic polymers, in order for the feeling of touch to be improved. Patent Document 4 is reported to have conducted a research about the improvement of a feeling upon use by combining a cationic polymer with a combination of dialkylene glycol which is an alkylene glycol ether of a short-chained alcohol, and an anionic surfactant. Yet this method is not enough to obtain sufficient foamability.

Any of the foregoing documents has yet to satisfy excellent foamability and excellent feeling upon use in parallel. Under such a circumstance, there has been a strong demand for the development of a skin or hair composition which is not only excellent in foamability, but also can enjoy a good feeling upon use in the process from washing to after drying.

[Patent Document 1] JP-A No. 2004-277685
[Patent Document 2] JP-A No. 11-12594
[Patent Document 3] JP-A No. 7-53991
[Patent Document 4] JP-A No. 4-108723

SUMMARY OF THE INVENTION

The present invention is relating to a skin or hair washing composition, containing the following components (A), (B) and (C):

(A) a compound represented by formula (1):

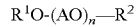
$$R^1O\text{-}(AO)_n\text{-}R^2$$

wherein $R^1$ represents a straight-chained or branched alkyl group or alkenyl group having 8 to 10 carbon atoms; AO represents an alkyleneoxy group having 2 to 4 carbon atoms; n, the average number of added moles, represents a number from 0.5 to less than 4.0; and $R^2$ represents a hydrogen atom or a methyl group, (B) a surfactant other than the component (A), and
(C) a cationic polymer, wherein the weight ratio of the component (A) and the component (C), (A)/(C), is from 0.5 to 60.

The present invention provides use of a composition containing the following components (A), (B) and (C), with the weight ratio of the component (A) and the component (C), (A)/(C), being from 0.5 to 60, as a skin or hair washing composition:

(A) a compound represented by formula (1):

$$R^1O\text{-}(AO)_n\text{-}R^2 \tag{1}$$

wherein $R^1$ represents a straight-chained or branched alkyl group or alkenyl group having 8 to 10 carbon atoms; AO represents an alkyleneoxy group having 2 to 4 carbon atoms; n, the average number of added moles, represents a number from 0.5 to less than 4.0; and $R^2$ represents a hydrogen atom or a methyl group, (B) a surfactant other than the component (A), and
(C) a cationic polymer.

The present invention also provides a method of washing the skin or the hair using a composition containing the following components (A), (B) and (C), with the weight ratio of the component (A) and the component (C), (A)/(C), being from 0.5 to 60:

(A) a compound represented by formula (1):

$$R^1O\text{-}(AO)_n\text{-}R^2 \tag{1}$$

wherein $R^1$ represents a straight-chained or branched alkyl group or alkenyl group having 8 to 10 carbon atoms; AO represents an alkyleneoxy group having 2 to 4 carbon atoms; n, the average number of added moles, represents a number from 0.5 to less than 4.0; and $R^2$ represents a hydrogen atom or a methyl group, (B) a surfactant other than the component (A), and
(C) a cationic polymer.

DETAILED DESCRIPTION OF THE INVENTION

The present invention provides a skin or hair washing composition, having excellent foamability and a good feeling upon use in the process from washing to after drying.

According to the present invention, a skin or hair washing composition, having excellent foamability and good feeling upon use in the process from washing to after-drying, is obtained.

In the formula (1) of the component (A), $R^1$ is a straight-chained or branched alkyl group or alkenyl group having 8 to 10 carbon atoms. From the viewpoint of odor reduction, a straight-chained alkyl group is preferred. From the viewpoint of foamability, $R^1$ is preferably a group having 8 carbon atoms, and in the case of mixed alkyls, it is preferable to have 50% by mole or more, more preferably 80% by mole or more, and even more preferably 98% by mole or more, of an alkyl having 8 carbon atoms.

In the formula (1) of the component (A), AO is an alkyleneoxy group having 2 to 4 carbon atoms, and is preferably a propyleneoxy group (hereinafter, referred to as PO) and/or an ethyleneoxy group (hereinafter, referred to as EO). PO and EO may be in a block arrangement or in a random arrangement, but are preferably in a block arrangement. From the viewpoint of odor reduction, a chain composed of PO and EO blocks that are arranged in the same order is preferred, and a chain composed solely of PO is a lot preferred.

For the compound of formula (1) of the component (A), the average number of added moles n represents a number from 0.5 to less than 4.0; and from the viewpoints of foamability and odor reduction, the number is 1.0 to 3.0, further 2.0 to 3.0, even more preferably 2.0 to 2.8, and much more preferably 2.0 to 2.5.

$R^2$ in the formula (1) represents a hydrogen atom or a methyl group, but is preferably a hydrogen atom.

It is preferable, from the viewpoints of foamability and economic efficiency, that the component (A) is contained in the washing composition in an amount of 0.1 to 20% by weight, more preferably 0.3 to 10% by weight, and even more preferably 0.5 to 5% by weight.

The surfactant of the component (B) is at least one surfactant selected from the group consisting of anionic surfactants, nonionic surfactants, amphoteric surfactants and cationic surfactants, and specifically, the following may be mentioned.

The anionic surfactants are preferably sulfuric acid-based, sulfonic acid-based, carboxylic acid-based, phosphoric acid-based and amino acid-based surfactants, and examples thereof include alkyl sulfates, polyoxyalkylene alkyl ether sulfates, polyoxyalkylene alkenyl ether sulfates, sulfosuccinic acid alkyl ester salts, polyoxyalkylene sulfosuccinic acid alkyl ester salts, polyoxyalkylene alkyl phenyl ether sulfates, alkanesulfonates, acylisethionate, acyl methyl taurate, higher fatty acid salts, polyoxyalkylene alkyl ether acetates, alkyl phosphates, polyoxyalkylene alkyl ether phosphates, acyl glutamates, alanine derivatives, glycine derivatives, arginine derivatives and the like.

Among these, polyoxyethylene alkyl ether sulfates, polyoxyethylene alkenyl ether sulfates, alkyl sulfates, higher fatty acid salts, polyoxyalkylene alkyl ether acetates, alkyl phosphates and polyoxyalkylene alkyl ether phosphates are preferred, and those represented by formula (3) or (4) are a lot preferred:

[Formula 3]

$$R^3-O(CH_2CH_2O)_pSO_3M \quad (3)$$

[Formula 4]

$$R^4-OSO_3M \quad (4)$$

wherein $R^3$ represents an alkyl group or alkenyl group having 10 to 18 carbon atoms; $R^4$ represents an alkyl group having 10 to 18 carbon atoms; M represents an alkali metal, an alkaline earth metal, ammonium, an alkanolamine or a basic amino acid; and p is an average number of added moles of ethylene oxide, and represents a number from 1 to 5.

Examples of the nonionic surfactant include polyoxyalkylene sorbitan fatty acid esters, polyoxyalkylene sorbite fatty acid esters, polyoxyalkylene glycerin fatty acid esters, polyoxyalkylene fatty acid esters, polyoxyalkylene alkyl ethers, polyoxyalkylene alkyl phenyl ethers, polyoxyalkylene (hydrogenated) castor oils, sucrose fatty acid esters, polyglycerin alkyl ethers, polyglycerin fatty acid esters, fatty acid alkanolamides, alkyl glycosides and the like. Among these, polyoxyalkylene alkyl ethers, alkyl glycosides, polyoxyalkylene C8-C20 fatty acid esters, polyoxyethylene sorbitan fatty acid esters, polyoxyethylene hydrogenated castor oils, and fatty acid alkanolamides are preferred. Preferred examples of the polyoxyalkylene alkyl ethers include polyoxyethylene alkyl ethers, polyoxypropylene alkyl ethers, and polyoxyethylene.polyoxypropylene alkyl ethers. Preferred examples of the alkyl glycosides include those having an alkyl having 8 to 14 carbon atoms and having a degree of sugar (glucose) condensation of 1 to 2. The fatty acid alkanolamides are preferably those having an acyl group having 8 to 18 carbon atoms, and more preferably 10 to 16 carbon atoms, and may be any of monoalkanolamides and dialkanolamides. However, an alkanolamide having a hydroxyalkyl group having 2 to 3 carbon atoms is preferred. Specific examples of the fatty acid alkanolamides include oleic acid diethanolamide, palm kernel oil fatty acid diethanolamide, coconut oil fatty acid diethanolamide, lauric acid diethanolamide, polyoxyethylene coconut oil fatty acid monoethanolamide, coconut oil fatty acid monoethanolamide, lauric acid monoisopropanolamide, lauric acid monoethanolamide, palm kernel oil fatty acid methyl ethanolamide, coconut oil fatty acid methyl ethanolamide and the like.

Examples of the amphoteric surfactants include betaine-based surfactants, amine oxide surfactants and the like. Among these, betaine-based surfactants such as imidazoline-based betaine, alkyl dimethyl aminoacetic acid betaine, fatty acid amide propyl betaine and sulfobetaine; and amine oxide surfactants such as alkyl dimethylamine oxide, are more preferred, and alkyl carboxymethyl hydroxy ethyl imidazolium betaine, fatty acid amide propyl betaine; sulfobetaines such as alkyl hydroxy sulfobetaine, alkyl sulfobetaine, fatty acid amide propyl hydroxy sulfobetaine and fatty acid amide propyl sulfobetaine; and alkyl dimethylamine oxides are even more preferred. Among them, sulfobetaines such as alkyl hydroxy sulfobetaine, alkyl sulfobetaine, fatty acid amide propyl hydroxy sulfobetaine and fatty acid amide propyl sulfobetaine are preferred, for example, from the viewpoint of the performance of not having the foamability impaired even in the presence of dirt, in the case of a skin or hair washing composition where excellent foamability are required even in the presence of dirt, that is, from the viewpoints of foamability and resistance to dirt, and from the viewpoint of thickening properties. Most preferred is alkyl hydroxy sulfobetaine. The fatty acid amide propyl betaine and alkyl hydroxy sulfobetaine preferably have an alkyl having 8 to 18 carbon atoms, and more preferably 10 to 16 carbon atoms, and, lauric acid amide propyl betaine, palm kernel oil fatty acid amide propyl betaine, coconut oil fatty acid amide propyl betaine, lauryl hydroxy sulfobetaine, lauryl sulfobetaine, coconut oil fatty acid amide propyl hydroxy sulfobetaine, coconut oil fatty acid amide propyl sulfobetaine and the like are preferred. Among them, lauryl hydroxy sulfobetaine is most preferred. The alkyl dimethylamine oxides preferably have an alkyl group having 8 to 18 carbon atoms, and more preferably 10 to 16 carbon atoms, and, lauryldimethylamine oxide and myristyl dimethylamine oxide are preferred.

As an example of the cationic surfactants, a quaternary ammonium salt represented by the following formula (5), as described in JP-A No. 2000-178146:

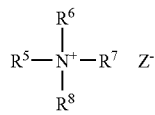

(5)

wherein at least one of $R^5$, $R^6$, $R^7$ and $R^8$ represents a straight-chained or branched alkyl group or alkenyl group, which may be substituted with an alkoxy group having 12 to 28 carbon atoms in total, and preferably a straight-chained or branched alkoxy group having 16 to 28 carbon atoms in total, an alkenyloxy group, an alkanoylamino group, an alkenoylamino group, an alkanoyl group or an alkanoyloxy group; the others each represent a benzyl group, an alkyl group having 1 to 5 carbon atoms, a hydroxyalkyl group or a polyoxyethylene group having a total number of added moles of 10 or less; and $Z^-$ represents a halogen ion or an organic anion selected from, for example, acetate, citrate, lactate, glycolate, phosphate, nitrate, sulfonate, sulfate and alkylsulfate groups.

Preferred examples of the compound (5) include those compounds wherein at least one of $R^5$, $R^6$, $R^7$ and $R^8$ represents an alkyl group which may be substituted with an alkoxy group having 8 to 22 carbon atoms, and the others each represent a methyl group, an ethyl group or a benzyl group. More preferred examples thereof include mono-long-chained alkyl trimethylammonium chloride such as stearyl trimethylammonium chloride or octadecyloxypropyl trimethylammonium chloride; di-long-chained alkyl dimethylammonium chloride such as distearyl dimethylammonium chloride or branched dialkyl dimethylammonium chloride; and the like.

The surfactant of the component (B) is preferably at least one surfactant selected from the group consisting of anionic surfactants, nonionic surfactants and amphoteric surfactants, from the viewpoint of foamability.

The component (B) is preferably contained in the washing composition in a proportion of 3 to 50% by weight, more preferably 5 to 30% by weight, and even more preferably 10 to 30% by weight, from the viewpoints of foamability and economic efficiency.

The weight ratio of the components (A) and (B), (A)/(B), is preferably 0.005 to 1, more preferably 0.01 to 1, even more preferably 0.02 to 0.5, and even more preferably 0.05 to 0.5, from the viewpoints of foamability and economic efficiency.

The cationic polymer of the component (C) may be exemplified by at least one selected from the group consisting of the following (a) to (d):

(a) a cationic group-containing copolymer comprising, as essential constituent monomers, at least one nonionic group-containing vinyl monomer represented by formula (I) or (II), at least one cationic group-containing vinyl monomer represented by formula (III) or (IV), and at least one crosslinkable vinyl monomer having at least two groups selected from a vinyl group, an acryloyl group, a methacryloyl group and an allyl group in the molecule, and obtained by radical polymerizing the essential constituent monomers:

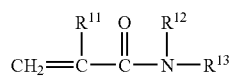

(I)

wherein $R^{11}$ represents a hydrogen atom or a methyl group; and $R^{12}$ and $R^{13}$, which may be identical or different, each represent a hydrogen atom or a straight-chained or branched alkyl group or alkenyl group having 1 to 4 carbon atoms,

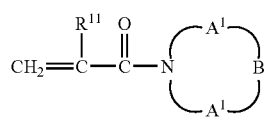

(II)

wherein $R^{11}$ has the same meaning as described above; $A^1$ and $A^2$, which may be identical or different, represents a group represented by formula: —$(CH_2)m$— (wherein m represents an integer from 2 to 6); and B represents —O— or a —$CH_2$— group,

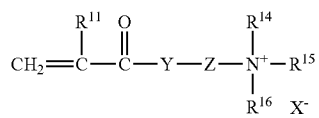

(III)

wherein $R^{11}$ has the same meaning as described above; $R^{14}$ and $R^{15}$, which may be identical or different, each represent an alkyl group or alkenyl group having 1 to 4 carbon atoms; $R^{16}$ represents a hydrogen atom or an alkyl group having 1 to 4 carbon atoms; Y represents —O—, —NH—, —$CH_2$— or —O—$CH_2CH(OH)$—; Z represents a straight-chained or branched alkylene group having 1 to 4 carbon atoms (provided that when Y is —$CH_2$—, the alkylene group has 0 to 3 carbon atoms); and X represents a conjugate base of an acid, a halogen atom or an alkyl sulfate group having 1 to 4 carbon atoms,

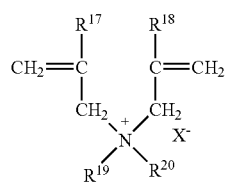

(IV)

wherein $R^{17}$ and $R^{18}$, which may be identical or different, each represent a hydrogen atom or a methyl group; $R^{19}$ and $R^{20}$, which may be identical or different, each represent a hydrogen atom or an alkyl group having 1 to 4 carbon atoms; and X has the same meaning as described above;

(b) a cationized cellulose derivative;

(c) a cationized guar gum derivative; and (d) a diallyl quaternary ammonium salt polymer or a diallyl quaternary ammonium salt/acrylamide copolymer.

The (a) cationic group-containing copolymer of the component (C) will be described in detail in the following.

(i) Nonionic Group-Containing Vinyl Monomer

Specific examples of the monomer represented by formula (I) include (meth)acrylamide, N-methyl (meth)acrylamide, N,N-dimethyl (meth)acrylamide, N,N-diethyl (meth)acrylamide, N-n-propyl (meth)acrylamide, N-isopropyl (meth)acrylamide, N-t-butyl (meth)acrylamide, N-isobutyl (meth)acrylamide, N-hydroxypropyl (meth)acrylamide and the like. Examples of the monomer represented by formula (II) include N-(meth)acryloylmorpholine and the like.

(ii) Cationic Group-Containing Vinyl Monomer

Specific examples of the monomer represented by formula (III) include acid neutralization products obtained by neutralizing a (meth)acrylic acid ester or (meth)acrylamide having a dialkylamino group, such as dimethylaminoethyl (meth)acrylate, diethylaminoethyl (meth)acrylate, dipropylaminoethyl (meth)acrylate, diisopropylaminoethyl (meth)acrylate, dibutylaminoethyl (meth)acrylate, diisobutylaminoethyl (meth)acrylate, di-t-butylaminoethyl (meth)acrylate, dimethylaminopropyl (meth) acrylamide, diethylaminopropyl (meth) acrylamide, dipropylaminopropyl (meth) acrylamide, diisopropylaminopropyl (meth) acrylamide, dibutylaminopropyl (meth) acrylamide, diisobutylaminopropyl (meth) acrylamide or di-t-butylaminopropyl (meth) acrylamide, with an acid; or quaternary ammonium salts obtained quaternizing the (meth)acrylic acid ester or (meth)acrylamide having a dialkylamino group, with a quaternizing agent.

Specific examples of the monomer represented by formula (IV) include diallyl quaternary ammonium salts such as dimethyl diallyl ammonium chloride and diethyl diallyl ammonium chloride.

Preferred examples of the acid used for obtaining the acid neutralization products include inorganic acids such as hydrochloric acid, sulfuric acid, nitric acid and phosphoric acid; organic acids having 1 to 22 carbon atoms in total, such as acetic acid, formic acid, maleic acid, fumaric acid, citric acid, tartaric acid, adipic acid, sulfamic acid, toluenesulfonic acid, lactic acid, pyrrolidine-2-carboxylic acid, succinic acid, propionic acid and glycolic acid; and the like. Preferred examples of the quaternizing agent used for obtaining the quaternary ammonium salts include alkyl halides having 1 to 8 carbon atoms, such as methyl chloride, ethyl chloride, methyl bromide and methyl iodide; and general alkylating agents such as dimethyl sulfate, diethyl sulfate and di-n-propyl sulfate.

Among the monomers represented by the formula (III) or (IV), preferred examples include quaternary ammonium salts obtained by quaternizing dimethylaminoethyl (meth)acrylate, diethylaminoethyl (meth)acrylate, dimethylaminopropyl (meth)acrylamide or diethylaminopropyl (meth)acrylamide, with the above-mentioned quaternizing agent; and dimethyl diallyl ammonium chloride. Here, the acid neutralization product monomers have defects such as that the neutralized acid undergoes dissociation in the pH environment of the system, and has changes in the polymer structure, thus having low stability in viscosity. From this point of view, quaternary ammonium salt type monomers are more preferred.

(iii) Crosslinkable Vinyl Monomer

Examples of the crosslinkable vinyl monomer include (meth)acrylic acid esters of polyhydric alcohols, such as ethylene glycol di(meth)acrylate, diethylene glycol di(meth)acrylate, polyethylene glycol di(meth)acrylate, propylene glycol di(meth)acrylate, dipropylene glycol di(meth)acrylate, polypropylene glycol di(meth)acrylate, 1,2-butylene glycol di(meth)acrylate, 1,3-butylene glycol di(meth)acrylate, neopentyl glycol di(meth)acrylate, glycerin di(meth)acrylate, glycerin tri(meth)acrylate, trimethylolpropane tri(meth)acrylate and pentaerythritol tetra(meth)acrylate; acrylamides such as N-methylallyl acrylamide, N-vinylacrylamide, N,N'-methylenebis(meth)acrylamide and bisacrylamide acetic acid; divinyl compounds such as divinylbenzene, divinyl ether and divinyl ethylene urea; polyallyl compounds such as diallyl phthalate, diallyl maleate, diallylamine, triallylamine, triallylammonium salts, allyl etherification products of pentaerythritol, and allyl etherification products of sucrose having at least two allyl ether units in the molecule; (meth) acrylic acid esters of unsaturated alcohols, such as vinyl (meth)acrylate, allyl (meth)acrylate, 2-hydroxy-3-acryloyloxypropyl (meth)acrylate, and 2-hydroxy-3-acryloyloxypropyl (meth)acrylate; and the like.

Among these crosslinkable monomers, ethylene glycol di(meth)acrylate, polyethylene glycol di(meth)acrylate, divinylbenzene, pentaerythritol triallyl ether, and pentaerythritol tetraallyl ether are preferred.

(iv) Other Vinyl Monomers

The (a) cationic group-containing copolymer of the component (C) can comprise, in addition to the above-described three types of vinyl monomers as the essential constituent units, another vinyl monomer which is capable of copolymerizing with these three vinyl monomers, as a constituent component. Examples of the other vinyl monomer include (meth)acrylic acid derivatives such as methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, n-pentyl (meth)acrylate, neopentyl (meth)acrylate, cyclopentyl (meth)acrylate, n-hexyl (meth)acrylate, cyclohexyl (meth)acrylate, n-octyl (meth)acrylate, isooctyl (meth)acrylate, 2-ethylhexyl (meth)acrylate, n-decyl (meth)acrylate, isodecyl (meth)acrylate, lauryl (meth)acrylate, tridecyl (meth)acrylate, stearyl (meth)acrylate, isostearyl (meth)acrylate, behenyl (meth)acrylate, phenyl (meth)acrylate, toluoyl (meth)acrylate, xylyl (meth)acrylate, benzyl (meth)acrylate, 2-ethoxyethyl (meth)acrylate, 2-butoxy (meth)acrylate, 2-phenoxy (meth)acrylate, 3-methoxypropyl (meth)acrylate and 3-ethoxypropyl (meth)acrylate; and the like.

These other vinyl monomers are preferably used in an amount of 30% by weight or less, and more preferably 15% by weight or less, based on the total amount of the monomers constituting the cationic group-containing copolymer.

(v) Cationic Group-Containing Copolymer

A preferred mixing ratio between a nonionic group-containing vinyl monomer ($a_1$) and a cationic group-containing vinyl monomer ($a_2$), which are monomers forming a cationic group-containing copolymer, ($a_1$)/($a_2$) by moles, is 2/98 to 98/2, and more preferably 40/60 to 97/3. If the molar ratio is high, manifestation of thixotropicity is facilitated, and if the molar ratio is small, it becomes easy to maintain the viscosity at a low shear rate. However, it is preferable that the molar ratio falls within the above-mentioned range, in view of manifesting both properties.

The proportion of the crosslinkable vinyl monomer ($a_3$) is preferably 0.002 to 5% by weight, and more preferably 0.0025 by weight or more and less than 0.1% by weight, based on the total amount of monomers. If the proportion of the monomer ($a_3$) is 0.002% by weight or more, the viscosity of the hydrogel formed from the cationic group-containing copolymer is sufficient. If the proportion is 5% by weight or less, the texture of the hydrogel is soft and velvety.

As a preferred embodiment of the (a) cationic group-containing copolymer of the component (C) of the present invention, there may be mentioned an N,N-dimethylaminoethyl methacrylic acid diethyl sulfate-N,N-dimethylacrylamide-dimethacrylic acid polyethylene glycol copolymer represented by the following formula:

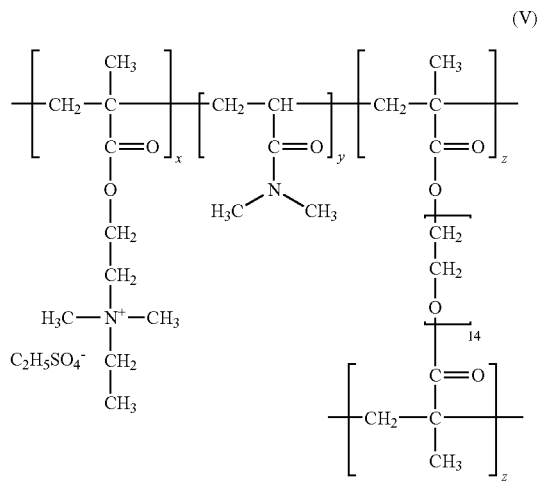

(V)

wherein x/y by moles is 1/9 to 5/5, and (x+y+z)/z is 1/0.1 to 1/0.002.

For example, there may be mentioned Sofcare KG-301W (manufactured by Kao Corp.) or Sofcare KG-101E (manufactured by Kao Corp.), as commercially available products.

The (b) cationized cellulose derivative of the component (C) will be described in detail in the following.

The (b) cationized cellulose derivative is preferably represented by the following formula (VI):

(VI)

In the formula (VI), A represents a residue of an anhydroglucose unit; a is an integer from 50 to 20000; and each of $R^{21}$ represents a substituent represented by the following formula (VII):

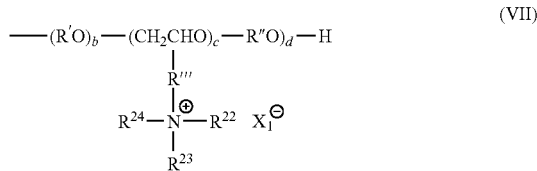

(VII)

wherein R' and R" each represent an alkylene group having 2 or 3 carbon atoms; b represents an integer from 0 to 10; c represents an integer from 0 to 3; d represents an integer from 0 to 10; R''' represents an alkylene or hydroxyalkylene group having 1 to 3 carbon atoms; $R^{22}$, $R^{23}$ and $R^{24}$, which may be identical or different, each represent an alkyl group, aryl group or aralkyl group having up to 10 carbon atoms, or $R^{22}$, $R^{23}$ and $R^{24}$ may form a heterocyclic ring together with the nitrogen atom in the formula; and $X_1$ represents an anion (chloride, bromide, iodide, sulfate, sulfonate, methylsulfate, phosphate, nitrate or the like).

The degree of cation substitution of the cationized cellulose is 0.01 to 1, that is, the average value of c per anhydroglucose unit is 0.01 to 1, and preferably 0.02 to 0.5. The sum of b+d is 1 to 3 on the average. A degree of substitution of 0.01 or less is not sufficient, whereas a degree of substitution of 1 or more may be adopted. However, from the viewpoint of reaction yield, the degree of substitution is preferably 1 or less. For example, a compound wherein $R^{22}$, $R^{23}$ and $R^{24}$ are all $CH_3$ groups, or two of them are short-chained alkyl groups such as $CH_3$ group, with the other one being a long-chained alkyl group having 10 to 20 carbon atoms, is preferred. Molecular weight of the cationized cellulose used herein is about between 100,000 and 8,000,000.

For example, there may be mentioned Poise C-80H (manufactured by Kao Corp.) or Polymer JR-400 (manufactured by Dow Chemical Company), as commercially available products.

The (c) cationized guar gum derivative of the component (C) will be described in detail in the following.

The (c) cationized guar gum derivative is preferably represented by the following formula (VIII):

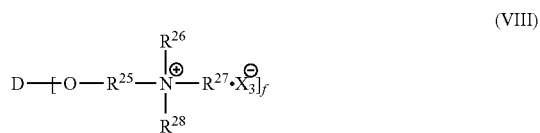

(VIII)

In the formula (VIII), D represents a guar gum residue; $R^{25}$ represents an alkylene group or hydroxyalkylene group; $R^{26}$, $R^{27}$ and $R^{28}$, which may be identical or different, each represent an alkyl group, aryl group or aralkyl group having 10 or less carbon atoms, or $R^{26}$, $R^{27}$ and $R^{28}$, may be form a heterocyclic ring together with the nitrogen atom in the formula; $X_3$ represents an anion (chloride, bromide, iodide, sulfate, sulfonate, methylsulfate, phosphate, nitrate or the like); and f represents a positive integer.

The degree of cation substitution of the cationized guar gum derivative is preferably 0.01 to 1, and much preferably, a derivative having 0.02 to 0.5 cation groups introduced into a sugar unit, is preferred. Cationic polymers of this type are described in JP-B No. 58-35640, JP-B No. 60-46158 and JP-A No. 58-53996. For example, commercially available products are marketed under the trade name of Jaguar from Rhodia Inc., and there may be mentioned Jaguar C-13C and the like.

The (d) diallyl quaternary ammonium salt polymer or diallyl quaternary ammonium salt/acrylamide copolymer of the component (C) will be described in detail in the following.

The (d) diallyl quaternary ammonium salt polymer or diallyl quaternary ammonium salt/acrylamide copolymer is preferably represented by the following formula (IX) or (X):

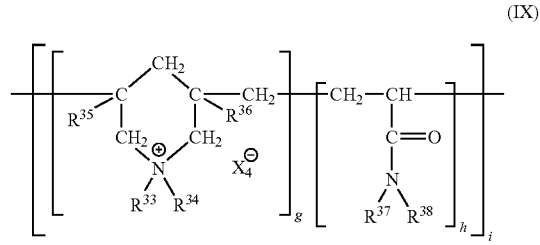

(IX)

-continued

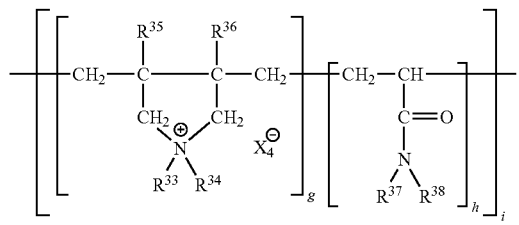

In the formulas (IX) and (X), $R^{33}$ and $R^{34}$, which may be identical or different, each represent a hydrogen atom, an alkyl group (having 1 to 18 carbon atoms), a phenyl group, an aryl group, a hydroxyalkyl group, an amidoalkyl group, a cyanoalkyl group, an alkoxyalkyl group, or a carboalkoxyalkyl group; $R^{35}$, $R^{36}$, $R^{37}$ and $R^{38}$, which may be identical or different, each represent a hydrogen atom, a lower alkyl group (having 1 to 3 carbon atoms), or a phenyl group; $X_4$ represents an anion (chloride, bromide, iodide, sulfate, sulfonate, methylsulfate, nitrate or the like); g represents an integer from 1 to 50; h represents an integer from 0 to 50; and i represents an integer from 150 to 8,000.

Molecular weight of the diallyl quaternary ammonium salt/acrylamide copolymer may be in the range of about 30,000 to 2,000,000, and preferably 100,000 to 1,000,000.

For example, commercially available products are marketed under the trade name Mercoat from Nalco Company, and there may be mentioned Mercoat 100, Mercoat 550 and the like.

From the viewpoint of the sense of touch, (a) a cationic group-containing copolymer, (c) a cationized guar gum derivative and (d) a diallyl quaternary ammonium salt polymer or diallyl quaternary ammonium salt/acrylamide copolymer are preferred as the component (C), while (a) a cationic group-containing copolymer and (d) a diallyl quaternary ammonium salt polymer or diallyl quaternary ammonium salt/acrylamide copolymer are more preferred, and (a) a cationic group-containing copolymer is much preferred.

One or more species can be used as the component (C). The content of the component (C) in the skin or hair washing composition is preferably 0.01 to 5% by weight, more preferably 0.05 to 1% by weight, and even more preferably 0.1 to 0.5% by weight, based on the total composition, from the viewpoints of the quality of foam, the sense of touch and the conditioning effect.

The weight ratio of the components (A) and (C), (A)/(C), is 0.5 to 60 from the viewpoints of foamability and the sense of touch, but the ratio is preferably 1 to 40, more preferably 1 to 30, much preferably 1 to 20, and most preferably 1 to 10.

The skin or hair washing composition of the present invention can contain oily components.

Examples of the oily components include higher alcohols, silicones, as well as ester oils, hydrocarbons, glycerides, plant oils, animal oils, lanolin derivatives, higher fatty acid esters and the like. Higher alcohols, ester oils and/or silicones are preferred, and higher alcohols and/or silicones are much preferred.

The skin or hair washing composition of the present invention can also appropriately contain glycerin, a moisturizer, a cationic polymer other than the component (C), a polysaccharide, a polypeptide, a pearlizing agent, a solvent, a liquid crystal forming base, a colorant, a fragrance, a propellant, a chelating agent such as edetate or citrate, a pH adjusting agent, an antiseptic, an anti-dandruff, and the like. The anti-dandruff may be exemplified by zinc pyrithione, piroctone olamine or the like.

The skin or hair washing composition of the present invention can be produced according to a standard method. The formulation is not particularly limited, and can be in any form, such as liquid, foam, paste, cream, solid or powder. However, the formulation is preferably in the form of liquid, paste or cream, and much preferably in the form of liquid. In the case of preparing the composition in a liquid form, it is preferable to use water, polyethylene glycol or the like as the liquid medium, and the amount of water to be incorporated is preferably 10 to 80% by weight of the total composition.

The pH of the skin or hair washing composition of the present invention is, in the case of preparing into a 20-fold dilution, preferably adjusted to 4 to 10, and much preferably 5 to 9, at 25° C.

The skin or hair washing composition of the present invention can be prepared according to a standard method, and for example, can be prepared into a body cleanser such as hair shampoo, body shampoo, facial cleanser or hand-wash.

EXAMPLES

Example 1

Hair shampoos as indicated in Table 3 were prepared according to a standard method, using the alkylene glycol ethers 1 to 9 indicated in Table 1 and Table 2 as the surfactant, and the hair shampoos were subjected to an evaluation of the foamability, feeling of foam, finger-combability during rinsing, and combability and softness of hair after drying, by the following methods. The results are presented in Table 3.

<Methods of Evaluation>

To 20 g (20 cm) of bleached hair of Japanese women, 1 g of shampoo was applied, and foams were generated for 30 seconds. At this time point, a panel of five experts evaluated the foamability, feeling of foam, finger-combability during rinsing, and combability and softness of hair after drying, on the basis of the following criteria.

1) Foamability
4: Very good foamability
3: Good foamability
2: Normal foamability
1: Poor foamability 2) Feeling of Foam
4: Very good feeling of touch with creamy quality of foam
3: Good feeling of touch with normal quality of foam
2: Slightly poor feeling of touch with normal quality of foam
1: Poor feeling of touch with rough quality of foam 3) Finger-Combability During Rinsing
4: Very good finger-combability with no friction
3: Good finger-combability with weak friction
2: Slightly poor finger-combability with slightly strong friction
1: Poor finger-combability with strong friction 4) Combability after Drying
4: Very smooth with good combability
3: Generally smooth, although some entanglement is observed when combing 2: Noticeable entanglement exists when combing
1: Poor combability, and entanglement exists to a large extent 5) Softness of Hair after Drying
4: Very soft and flexible
3: Soft
2: Somewhat less soft
1: Stiff Average points were determined from the evaluation results of all the five experts, and an average value of 3.6 or more was rated as "A", an average value of 2.6 to 3.4 was rated as "B", an average value of 1.6 to 2.4 was rated as "C", and an average value of 1.4 or less was rated as "D".

6) Test for Resistance to Dirt

To 15 g (20 cm) of the hair of Japanese women, soaked in 15 g of ion-exchanged water and coated with 0.05 mL of lanolin (manufactured by Yamakei Sangyo Co., Ltd.) as a dirt component, 0.5 mL each of the hair shampoos indicated in Table 3 was applied, and foam was generated for 25 seconds. The generated foam was taken into a graduated cylinder having a diameter of 5 cm, and the amount of foam (mL) was measured.

TABLE 1

| R1O-(AO)n-R2 | R1* | R2 | (AO)n |
|---|---|---|---|
| Alkylene glycol ether 1 | C8 | H | (PO) 2.3 |
| Alkylene glycol ether 2 | C8 | H | (EO) 2 |
| Alkylene glycol ether 3 | 2-Ethylhexyl | H | (EO) 2.5 |
| Alkylene glycol ether 4 | C8/C10(Molar ratio: 1/1) | H | (PO) 1.8 |
| Alkylene glycol ether 8 | C8 | H | (PO) 2.7 |
| Alkylene glycol ether 9 | C8 | H | (EO) 2.7 |

*C8: n-octyl, C10: n-decyl

TABLE 2

| R1O-(AO)n-R2 | R1* | R2 | (AO)n |
|---|---|---|---|
| Alkylene glycol ether 5 | C12 | H | (EO) 2(PO) 2 (EO) 3 |
| Alkylene glycol ether 6 | C10 | H | (PO) 1 (EO) 6 |
| Alkylene glycol ether 7 | C3 | H | (PO) 2 |

*C12: n-dodecyl, C10: n-decyl, C3: n-propyl

TABLE 3

| Component | Hair shampoo Composition (% by weight) | Product of the invention ||||||||| 
|---|---|---|---|---|---|---|---|---|---|---|
| | | 1 | 2 | 3 | 4 | 5 | 6 | 7 | 8 | 9 |
| (A) | Alkylene glycol ether 1 | 1.0 | | | | 8.0 | 5.0 | 2.0 | 1.0 | |
| | Alkylene glycol ether 2 | | 1.0 | | | | | | | |
| | Alkylene glycol ether 3 | | | 1.0 | | | | | | |
| | Alkylene glycol ether 4 | | | | 1.0 | | | | | |
| | Alkylene glycol ether 8 | | | | | | | | | 1.0 |
| | Alkylene glycol ether 9 | | | | | | | | | |
| | Alkylene glycol ether 5 | | | | | | | | | |
| | Alkylene glycol ether 6 | | | | | | | | | |
| | Alkylene glycol ether 7 | | | | | | | | | |
| (B) | Sodium polyoxyethylene (EOp = 2) alkyl ether sulfate | 15.0 | 14.0 | 10.0 | 15.0 | 10.0 | 15.0 | | | |
| | Sodium polyoxyethylene (EOp = 1) alkyl ether sulfate | | | | | | | | 13.0 | 13.0 |
| | Alkyl polyglucoside[1)] | | | 3.0 | | | | | | |
| | Alkyl carboxymethyl hydroxyethyl imidazolinium betaine[2)] | | | | | | | 10.0 | | |
| | Lauryl hydroxy sulfobetaine | | | | | | | | 1.0 | |
| | Coconut oil fatty acid amide propyl betaine | | | | | | | 0.5 | | |
| | Lauryl dimethylamine oxide | | | | | 2.0 | | | | |
| (C) | Cationic polymer 1[3)] | 0.2 | 0.3 | | 0.3 | | | 0.5 | 0.2 | 0.3 |
| | Cationic polymer 3[4)] | 0.2 | | 0.1 | | 0.5 | | 0.1 | | |
| | Cationic polymer 4[5)] | 0.2 | 0.3 | | | | | | | |

TABLE 3-continued

|  |  |  |  |  |  |  |  |  |  |  |
|---|---|---|---|---|---|---|---|---|---|---|
|  | Cationic polymer 5[6] |  |  |  | 0.3 |  |  |  | 0.1 |  |
|  | Myristyl alcohol |  | 0.8 |  |  |  |  |  |  |  |
|  | Ethanol |  |  |  |  |  |  |  |  |  |
|  | pH adjusting agent | Adequate amount | Adequate amount | Adequate amount | Adequate amount | Adequate amount | Adequate amount | Adequate amount | Adequate amount | Adequate amount |
|  | Purified water | Balance | Balance | Balance | Balance | Balance | Balance | Balance | Balance | Balance |
|  | (A)/(C) | 1.7 | 3.3 | 3.3 | 2.5 | 26.7 | 10.0 | 4.0 | 2.5 | 3.3 |
|  | pH (20-fold dilution: 25° C.) | 6.5 | 6.5 | 6.2 | 7.2 | 6.0 | 6.0 | 6.8 | 6.0 | 6.8 |
| Evaluation results | Foamability | A | A | B | B | A | A | B | A | A |
|  | Resistance to dirt | 130 | 130 | 120 | 130 | — | — | — | 180 | 140 |
|  | Feeling of foam | A | A | A | B | A | A | A | A | A |
|  | Finger-combability during rinsing | A | B | A | A | B | B | A | A | A |
|  | Combability after drying | A | A | A | B | A | B | A | A | A |
|  | Softness after drying | A | B | B | A | A | A | B | A | B |

| Component | Hair shampoo Composition (% by weight) | Product of the invention | | | | | | | Comparative product | |
|---|---|---|---|---|---|---|---|---|---|---|
|  |  | 10 | 11 | 12 | 13 | 14 | 15 | 16 | 1 | 2 |
| (A) | Alkylene glycol ether 1 |  |  |  |  |  |  |  |  |  |
|  | Alkylene glycol ether 2 |  |  |  |  |  |  |  |  |  |
|  | Alkylene glycol ether 3 |  |  |  |  |  |  |  |  |  |
|  | Alkylene glycol ether 4 |  |  |  |  |  |  |  |  |  |
|  | Alkylene glycol ether 8 | 1.0 | 1.0 | 1.0 | 1.0 | 1.0 | 1.0 |  |  |  |
|  | Alkylene glycol ether 9 |  |  |  |  |  |  | 1.0 |  |  |
|  | Alkylene glycol ether 5 |  |  |  |  |  |  |  |  |  |
|  | Alkylene glycol ether 6 |  |  |  |  |  |  |  |  |  |
|  | Alkylene glycol ether 7 |  |  |  |  |  |  |  |  |  |
| (B) | Sodium polyoxyethylene (EOp = 2) alkyl ether sulfate |  |  |  |  |  |  |  | 14.0 | 14.0 |
|  | Sodium polyoxyethylene (EOp = 1) alkyl ether sulfate | 13.0 | 13.0 | 13.0 | 13.0 | 13.0 | 13.0 | 13.0 |  |  |
|  | Alkyl polyglucoside[1] |  |  |  |  |  |  |  |  |  |
|  | Alkyl carboxymethyl hydroxyethyl imidazolinium betaine[2] |  |  |  |  |  |  |  |  |  |
|  | Lauryl hydroxy sulfobetaine | 1.0 |  | 1.0 | 1.0 | 1.0 | 1.0 | 1.0 |  |  |
|  | Coconut oil fatty acid amide propyl betaine |  | 1.0 |  |  |  |  |  | 1.0 | 1.0 |
|  | Lauryl dimethylamine oxide |  |  |  |  |  |  |  |  |  |
| (C) | Cationic polymer 1[3] | 0.3 | 0.3 |  |  |  | 0.2 | 0.3 |  | 0.3 |
|  | Cationic polymer 3[4] |  |  |  |  | 0.3 | 0.1 |  |  |  |
|  | Cationic polymer 4[5] |  |  |  | 0.3 |  |  |  |  |  |
|  | Cationic polymer 5[6] |  |  | 0.3 |  |  | 0.1 |  |  |  |
|  | Myristyl alcohol |  |  |  |  |  |  |  |  |  |

TABLE 3-continued

|  | | | | | | | | | | |
|---|---|---|---|---|---|---|---|---|---|---|
| | Ethanol<br>pH adjusting agent<br>Purified water | Adequate amount<br>Balance | Adequate amount<br>Balance | Adequate amount<br>Balance | Adequate amount<br>Balance | Adequate amount<br>Balance | Adequate amount<br>Balance | Adequate amount<br>Balance | Adequate amount<br>Balance | Adequate amount<br>Balance |
| | (A)/(C) | 3.3 | 3.3 | 3.3 | 3.3 | 3.3 | 2.5 | 3.3 | — | — |
| | pH (20-fold dilution: 25° C.) | 6.8 | 6.8 | 6.8 | 6.8 | 6.8 | 6.2 | 6.2 | 6.5 | 6.5 |
| Evaluation results | Foamability | A | A | A | A | A | A | A | C | C |
| | Resistance to dirt | 180 | 150 | 160 | 190 | 150 | 180 | 160 | 100 | 90 |
| | Feeling of foam | A | A | A | B | B | A | A | C | C |
| | Finger-combability during rinsing | A | A | B | A | A | A | B | C | B |
| | Combability after drying | A | A | B | B | B | A | A | C | B |
| | Softness after drying | B | B | A | A | B | A | B | C | B |

| Component | Hair shampoo Composition (% by weight) | Comparative product | | | | | | | |
|---|---|---|---|---|---|---|---|---|---|
| | | 3 | 4 | 5 | 6 | 7 | 8 | 9 | 10 |
| (A) | Alkylene glycol ether 1 | | | | | | | 8.0 | |
| | Alkylene glycol ether 2 | 1.0 | | | | | | | |
| | Alkylene glycol ether 3 | | | | | | | | |
| | Alkylene glycol ether 4 | | | | | | | | |
| | Alkylene glycol ether 8 | | | | | | 1.0 | | 1.0 |
| | Alkylene glycol ether 9 | | | | | | | | |
| | Alkylene glycol ether 5 | | 1.0 | | | | | | |
| | Alkylene glycol ether 6 | | | 8.0 | | | | | |
| | Alkylene glycol ether 7 | | | | 5.0 | | | | |
| (B) | Sodium polyoxyethylene (EOp = 2) alkyl ether sulfate | 14.0 | 18.0 | 10.0 | 15.0 | | | 10.0 | |
| | Sodium polyoxyethylene (EOp = 1) alkyl ether sulfate | | | | | 13.0 | 13.0 | | 13.0 |
| | Alkyl polyglucoside[1] | | | | | | | | |
| | Alkyl carboxymethyl hydroxyethyl imidazolinium betaine[2] | | | | | | | | |
| | Lauryl hydroxy sulfobetaine | | | | | 1.0 | | | 1.0 |
| | Coconut oil fatty acid amide propyl betaine | | | | | | 2.0 | | |
| | Lauryl dimethylamine oxide | | 7.0 | 2.0 | | | | 2.0 | |
| (C) | Cationic polymer 1[3] | | | | | | | 0.1 | 3.0 |
| | Cationic polymer 3[4] | | | | 0.5 | | | | |
| | Cationic polymer 4[5] | | | | | | | | |
| | Cationic polymer 5[6] | | | | | | | 0.3 | |
| | Myristyl alcohol | | | | | | | | |

TABLE 3-continued

|  |  |  |  |  |  |  |  |  |  |
|---|---|---|---|---|---|---|---|---|---|
|  | Ethanol |  | 5.0 |  |  |  |  |  |  |
|  | pH adjusting agent | Adequate amount | Adequate amount | Adequate amount | Adequate amount | Adequate amount | Adequate amount | Adequate amount | Adequate amount |
|  | Purified water | Balance | Balance | Balance | Balance | Balance | Balance | Balance | Balance |
|  | (A)/(C) | — | — | — | — | — | — | 80.0 | 0.3 |
|  | pH (20-fold dilution: 25° C.) | 6.5 | 7.0 | 7.0 | 6. | 6.8 | 6.8 | 6.0 | 6.8 |
| Evaluation results | Foamability | A | B | B | C | A | B | B | C |
|  | Resistance to dirt | 120 | — | — | — | 150 | 140 | — | 80 |
|  | Feeling of foam | C | C | D | B | C | B | C | D |
|  | Finger-combability during rinsing | D | C | D | B | D | C | D | C |
|  | Combability after drying | D | D | D | C | D | C | D | C |
|  | Softness after drying | D | D | D | B | D | B | D | C |

[1] Mydol 10 (manufactured by Kao Corp.)
[2] Anhitol 20YB (manufactured by Kao Corp.)
[3] Sofcare KG101E (manufactured by Kao Corp.)
[4] Polymer JR-400 (manufactured by Dow Chemical Company)
[5] Jaguar C-13C (manufactured by Rhodia, Inc.)
[6] Mercoat 550 (manufactured by Nalco Company)

As shown in the results of Table 3, comparative product 2 prepared by adding a cationic polymer to comparative product 1, which has been prepared by conventional technology, has weak foamability, and has a feel of touch showing only a slight improvement (to a known level). Meanwhile, comparative product 3 containing a specific foam enhancer, which is the component (A) of the present invention, has good foamability, but is defective in the feeling of touch. When a cationic polymer is added to this comparative product 3 (i.e., product of the invention 2), the feeling of touch is remarkably improved. It is understood that when a cationic polymer is added to a specific foam enhancer, addition of a cationic polymer becomes more effective than in the case of adding a cationic polymer to a product of conventional technology (comparative product 1). Furthermore, those having the weight ratio of the components (A) and (C), (A)/(C), out of the range of 0.5 to 60 (comparative products 9 and 10), were defective in foamability or in the feeling of touch.

Example 2

Body shampoos as indicated in Table 4 were prepared according to a standard method, using the alkylene glycol ethers 1 to 9 indicated in Table 1 and Table 2 as the surfactant, and the body shampoos were subjected to an evaluation of the foamability, feeling of foam, ease of rinsing, and moist feeling after drying, by the following methods. The results are presented in Table 4.

<Methods of Evaluation>

A panel of five experts took 1 g of body shampoo in hands and washed their hands and arms, and during the washing, the experts evaluated the foamability, feeling of foam, ease of rinsing, and moist feeling after drying, on the basis of the following criteria.

1) Foamability
4: Very good foamability
3: Good foamability
2: Normal foamability
1: Poor foamability 2) Feeling of Foam
4: Very good feeling of touch with creamy quality of foam
3: Good feeling of touch with normal quality of foam
2: Slightly poor feeling of touch with normal quality of foam
1: Poor feeling of touch with rough quality of foam 3) Ease of Rinsing
4: Very good rinsability
3: Good rinsability
2: Slightly poor rinsability, and sliminess remains behind
1: Poor rinsability and strongly slimy.

4) Moist Feeling after Drying
4: Very moist, and dampness is felt
3: Moist
2: Moist feeling is insufficient
1: Crispy Average points were determined from the evaluation results of all the five experts, and an average value of 3.6 or more was rated as A, an average value of 2.6 to 3.4 was rated as B, an average value of 1.6 to 2.4 was rated as C, and an average value of 1.4 or less was rated as D.

5) Test for Resistance to Dirt
To the palms of hands wetted with tap water and coated with 0.1 mL of lanolin (manufactured by Yamakei Sangyo Co., Ltd.) as a dirt component, 1 g of the body shampoos indicated in Table 4 were taken, and foams were generated for 30 seconds. The generated foam was taken into a graduated cylinder having a diameter of 5 cm, and the amount of foam (mL) was measured.

TABLE 4

| Component | Body shampoo Composition (% by weight) | Product of the invention | | | | | | |
|---|---|---|---|---|---|---|---|---|
|  |  | 17 | 18 | 19 | 20 | 21 | 22 | 23 |
| (A) | Alkylene glycol ether 1 | 2.0 |  |  |  |  | 8.0 | 5.0 |
|  | Alkylene glycol ether 2 |  | 2.0 |  |  |  |  |  |

TABLE 4-continued

|   | | | | | | | | |
|---|---|---|---|---|---|---|---|---|
|   | Alkylene glycol ether 3 |  |  | 2.0 |  |  |  |  |
|   | Alkylene glycol ether 4 |  |  |  | 2.0 |  |  |  |
|   | Alkylene glycol ether 8 |  |  |  |  |  |  | 2.0 |
|   | Alkylene glycol ether 9 |  |  |  |  |  |  |  |
|   | Alkylene glycol ether 5 |  |  |  |  |  |  |  |
|   | Alkylene glycol ether 6 |  |  |  |  |  |  |  |
|   | Alkylene glycol ether 7 |  |  |  |  |  |  |  |
| (B) | Sodium polyoxyethylene (EOp = 2) alkyl ether sulfate | 5.0 | 14.0 |  |  | 10.0 | 15.0 |  |
|   | Sodium polyoxyethylene (EOp = 1) alkyl ether sulfate |  |  |  |  |  |  | 13.0 |
|   | Potassium alkylphosphate[1] | 20.0 | 18.0 |  |  |  |  |  |
|   | Polyoxyethylene (1) lauryl phosphate K salt/polyoxyethylene (1) dilauryl phosphate K salt[2] (monolauryl product/dilaury product = 80/20) |  |  |  |  |  |  |  |
|   | Potassium laurate |  |  |  | 18.0 |  |  |  |
|   | Lauryl hydroxy sulfobetaine |  |  |  |  |  |  | 2.0 |
|   | Coconut oil fatty acid amidopropyl betaine |  |  |  |  |  |  |  |
|   | Lauryl dimethylamine oxide |  |  |  |  | 2.0 |  |  |
| (C) | Cationic polymer 2[3] | 0.5 |  |  | 0.3 | 0.3 |  | 0.3 |
|   | Cationic polymer 3[4] |  | 0.5 |  |  |  | 0.5 |  |
|   | Cationic polymer 5[5] |  |  | 0.5 | 0.1 |  |  |  |
|   | Ethanol |  |  |  |  |  |  |  |
|   | pH adjusting agent | Adequate amount | Adequate amount | Adequate amount | Adequate amount | Adequate amount | Adequate amount | Adequate amount |
|   | Purified water | Balance | Balance | Balance | Balance | Balance | Balance | Balance |
|   | (A)/(C) | 4.0 | 4.0 | 4.0 | 5.0 | 26.7 | 10.0 | 6.7 |
|   | pH (20-fold dilution: 25° C.) | 6.5 | 6.5 | 6.2 | 7.2 | 6.0 | 6.0 | 6.5 |
| Evaluation results | Foamability | A | A | B | A | A | A | A |
|   | Resistance to dirt | 80 | 60 | 80 | 140 | — | 70 | 100 |
|   | Feeling of foam | A | A | B | A | A | A | A |
|   | Ease of rinsing | A | B | A | A | B | B | B |
|   | Softness after drying | A | A | B | B | A | A | B |

| Component | Body shampoo Composition (% by weight) | Product of the invention ||||| Comparative product ||
|---|---|---|---|---|---|---|---|---|
|   |   | 24 | 25 | 26 | 27 | 28 | 11 | 12 |
| (A) | Alkylene glycol ether 1 |  |  |  |  |  |  |  |
|   | Alkylene glycol ether 2 |  |  |  |  |  |  |  |
|   | Alkylene glycol ether 3 |  |  |  |  |  |  |  |

TABLE 4-continued

| Component | | | | | | | | |
|---|---|---|---|---|---|---|---|---|
| | Alkylene glycol ether 4 | | | | | | | |
| | Alkylene glycol ether 8 | 2.0 | 2.0 | 2.0 | 2.0 | | | |
| | Alkylene glycol ether 9 | | | | | 2.0 | | |
| | Alkylene glycol ether 5 | | | | | | | |
| | Alkylene glycol ether 6 | | | | | | | |
| | Alkylene glycol ether 7 | | | | | | | |
| (B) | Sodium polyoxyethylene (EOp = 2) alkyl ether sulfate | | | | | | 14.0 | 14.0 |
| | Sodium polyoxyethylene (EOp = 1) alkyl ether sulfate | 13.0 | | | | | | |
| | Potassium alkylphosphate[1] | | | | | | | |
| | Polyoxyethylene (1) lauryl phosphate K salt/polyoxyethylene (1) dilauryl phosphate K salt[2] (monolauryl product/dilaury product = 80/20) | | 16.0 | 16.0 | 16.0 | 16.0 | | |
| | Potassium laurate | | | | | | | |
| | Lauryl hydroxy sulfobetaine | | 2.0 | | 2.0 | 2.0 | | |
| | Coconut oil fatty acid amidopropyl betaine | 2.0 | | 2.0 | | | 2.0 | 2.0 |
| | Lauryl dimethylamine oxide | | | | | | | |
| (C) | Cationic polymer 2[3] | 0.3 | 0.8 | 0.8 | | | | |
| | Cationic polymer 3[4] | | | | | | | 0.5 |
| | Cationic polymer 5[5] | | | | 0.3 | 0.3 | | |
| | Ethanol | | | | | | | |
| | pH adjusting agent | Adequate amount | Adequate amount | Adequate amount | Adequate amount | Adequate amount | Adequate amount | Adequate amount |
| | Purified water | Balance | Balance | Balance | Balance | Balance | Balance | Balance |
| | (A)/(C) | 6.7 | 2.5 | 2.5 | 6.7 | 6.7 | — | — |
| | pH (20-fold dilution: 25° C.) | 6.5 | 6.5 | 6.5 | 6.0 | 6.0 | 6.5 | 6.5 |
| Evaluation results | Foamability | A | A | B | A | A | C | C |
| | Resistance to dirt | 70 | 130 | 90 | 120 | 110 | 60 | 50 |
| | Feeling of foam | A | A | A | B | B | C | B |
| | Ease of rinsing | B | A | A | A | A | C | C |
| | Softness after drying | B | A | B | A | B | C | B |

| Component | Body shampoo Composition (% by weight) | Comparative product | | | | | | |
|---|---|---|---|---|---|---|---|---|
| | | 13 | 14 | 15 | 16 | 17 | 18 | 19 |
| (A) | Alkylene glycol ether 1 | | | | | | 5.0 | 2.0 |
| | Alkylene glycol ether 2 | 2.0 | | | | | | |
| | Alkylene glycol ether 3 | | | | | | | |
| | Alkylene glycol ether 4 | | | | | | | |

TABLE 4-continued

|  |  | | | | | | | |
|---|---|---|---|---|---|---|---|---|
|  | Alkylene glycol ether 8 | | | | | | | |
|  | Alkylene glycol ether 9 | | | | | | | |
|  | Alkylene glycol ether 5 | | 1.0 | | | | | |
|  | Alkylene glycol ether 6 | | | 8.0 | | | | |
|  | Alkylene glycol ether 7 | | | | 5.0 | | | |
| (B) | Sodium polyoxyethylene (EOp = 2) alkyl ether sulfate | 14.0 | 18.0 | 10.0 | 15.0 | | 15.0 | 5.0 |
|  | Sodium polyoxyethylene (EOp = 1) alkyl ether sulfate | | | | | | | |
|  | Potassium alkylphosphate[1] | | | | | | | 20.0 |
|  | Polyoxyethylene (1) lauryl phosphate K salt/polyoxyethylene (1) dilauryl phosphate K salt[2] (monolauryl product/dilauryl product = 80/20) | | | | | 16.0 | | |
|  | Potassium laurate | | | | | | | |
|  | Lauryl hydroxy sulfobetaine | | | | | 2.0 | | |
|  | Coconut oil fatty acid amidopropyl betaine | | | | | | | |
|  | Lauryl dimethylamine oxide | | 7.0 | 2.0 | | | | |
| (C) | Cationic polymer 2[3] | | | | | | | 5.0 |
|  | Cationic polymer 3[4] | | | | 0.5 | | 0.08 | |
|  | Cationic polymer 5[5] | | | | | 0.3 | | |
|  | Ethanol | | 5.0 | | | | | |
|  | pH adjusting agent | Adequate amount | Adequate amount | Adequate amount | Adequate amount | Adequate amount | Adequate amount | Adequate amount |
|  | Purified water | Balance | Balance | Balance | Balance | Balance | Balance | Balance |
|  | (A)/(C) | — | — | — | — | — | 62.5 | 0.4 |
|  | pH (20-fold dilution: 25° C.) | 6.5 | 7.0 | 7.0 | 6.0 | 6.0 | 6.0 | 6.0 |
| Evaluation results | Foamability | B | B | B | C | B | B | D |
|  | Resistance to dirt | — | — | — | — | 80 | — | 25 |
|  | Feeling of foam | D | C | D | B | B | C | D |
|  | Ease of rinsing | C | C | C | D | C | B | D |
|  | Softness after drying | D | D | D | B | B | C | C |

[1] Prioly B-6500 (manufactured by Kao Corp.)
[2] The number within the parentheses represents the average number of added moles of ethylene oxide.
[3] Sofcare KG301E (manufactured by Kao Corp.)
[4] Polymer JR-400 (manufactured by Dow Chemical Company)
[5] Mercoat 550 (manufactured by Nalco Company)

From the results of Table 4, it is understood that the products of the invention had remarkable effects of using a specific foam enhancer and a cationic polymer in combination, just like in the case of the hair shampoos in Table 3.

Example 3

A hair shampoo having the following composition was produced.

| (Component) | (% by weight) |
|---|---|
| Alkylene glycol ether 1 | 0.7 |
| Sodium polyoxyethylene (1) lauryl ether sulfate* | 12.0 |
| Lauric acid monoethanol amide | 0.8 |
| Cationic polymer 1** | 0.2 |
| Cationic polymer 3*** | 0.2 |
| Silicone**** | 1.0 |
| Fragrance, methylparaben | Adequate amounts |
| Purified water | Balance |
| Total | 100.0 |

*The number within the parentheses represents the average number of added moles of ethylene oxide.
**Sofcare KG101E (manufactured by Kao Corp.)
***Poise C-150L (manufactured by Kao Corp.)
****Silicone BY22-060 (manufactured by Toray-Dow Corning Silicone Co., Ltd.)

This hair shampoo had good foamability, and good finger-combability in the process from washing to after drying, thus presenting an excellent feeling upon use.

Example 4

A body shampoo having the following composition was produced.

| (Component) | (% by weight) |
|---|---|
| Alkylene glycol ether 2 | 2.0 |
| Lauryl phosphate* | 30.0 |
| Cationic polymer 2** | 0.5 |
| Amidopropyl betaine*** | 2.0 |
| Glycerin | 3.0 |
| Fragrance, methylparaben | Adequate amounts |
| Purified water | Balance |
| Total | 100.0 |

*Prioly B-650D (manufactured by Kao Corp.)
**Sofcare KG301W (manufactured by Kao Corp.)
***Anhitol 20AB (manufactured by Kao Corp.)

This body shampoo had good foamability, a good quality of foam during washing, and moistened even after drying, thus presenting an excellent sense of use.

Example 5

A hair shampoo having the following composition was produced.

| (Component) | (% by weight) |
|---|---|
| Alkylene glycol ether 8 | 0.6 |
| Sodium polyoxyethylene (1) lauryl ether sulfate* | 12.0 |
| Palm oil fatty acid amidopropyl betaine | 1.2 |
| Lauryl hydroxy sulfobetaine | 0.6 |
| Cationic polymer 1** | 0.2 |
| Cationic polymer 4*** | 0.2 |
| Silicone**** | 2.0 |
| Fragrance, methylparaben | Adequate amounts |
| Purified water | Balance |
| Total | 100.0 |

*The number within the parentheses represents the average number of added moles of ethylene oxide.
**Sofcare KG101E (manufactured by Kao Corp.)
***Jaguar C-13C (manufactured by Rhodia, Inc.)
****Silicone BY22-014 (manufactured by Toray-Dow Corning Silicone Co., Ltd.)

This hair shampoo had good foamability and resistance to dirt, and had good finger-combability through a process from washing to after drying, thus presenting an excellent feeling upon use.

Example 6

A hair shampoo having the following composition was produced.

| (Component) | (% by weight) |
|---|---|
| Alkylene glycol ether 8 | 0.6 |
| Ammonium lauryl ether sulfate | 6.0 |
| Ammonium polyoxyethylene (3) lauryl ether sulfate* | 6.0 |
| Palm oil fatty acid monoethanol amide | 0.8 |
| Lauryl hydroxy sulfobetaine | 0.5 |
| Cationic polymer 5** | 0.4 |
| Silicone*** | 2.0 |
| Fragrance, methylparaben | Adequate amounts |
| Purified water | Balance |
| Total | 100.0 |

*The number within the parentheses represents the average number of added moles of ethylene oxide.
**Mercoat 550 (manufactured by Nalco Company)
***Silicone BY22-007 (manufactured by Toray-Dow Corning Silicone Co., Ltd.0

This hair shampoo had good foamability and resistance to dirt, and had good finger-combability in the process from washing to after drying, thus presenting an excellent feeling upon use.

What is claimed is:
1. A skin or hair washing composition, comprising the following components (A), (B) and (C):
(A) a compound represented by formula (1):

$$R^1O\text{-}(AO)_n\text{---}R^2 \quad (1)$$

wherein $R^1$ represents a straight-chained or branched alkyl group or alkenyl group having 8 carbon atoms; AO represents an alkyleneoxy group having 2 to 4 carbon atoms; n, the average number of added moles, represents a number from 0.5 to less than 4.0; and $R^2$ represents a hydrogen atom;
(B) a surfactant selected from the group consisting of a polyoxyethylene alkyl ether sulfate, a polyoxyethylene alkenyl ether sulfate, an alkyl sulfate, a higher fatty acid salt, a polyoxyalkylene alkyl ether acetate, an alkyl phosphate, a polyoxyalkylene alkyl ether phosphate, a polyoxolkylene alkyl ether, an alkyl polyglucoside, a polyoxyalkylene C8-C20 fatty acid ester, a polyoxyalkylene sorbitan fatty acid ester, a polyoxyethylene hydrogenated castor oil, a fatty acid alkanolamide, a betaine-based surfactant, and an amine oxide surfactant;

(C) a cationic polymer, wherein the weight ratio of the component (A) and the component (C), (A)/(C), is from 0.5 to 30.

2. The skin or hair washing composition according to claim 1, wherein the component (C) is at least one selected from the group consisting of (a) a cationic group-containing copolymer comprising, as essential constituent monomers, at least one nonionic group-containing vinyl monomer represented by formula (I) or (II), at least one cationic group-containing vinyl monomer represented by formula (III) or (IV), and at least one crosslinkable vinyl monomer having at least two groups selected from a vinyl group, an acryloyl group, a methacryloyl group and an allyl group in the molecule, and obtained by radical polymerizing these essential constituent monomers:

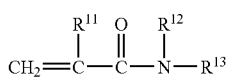
(I)

wherein $R^{11}$ represents a hydrogen atom or a methyl group; and $R^{12}$ and $R^{13}$, which may be identical or different, each represent a hydrogen atom or a straight-chained or branched alkyl group or alkenyl group having 1 to 4 carbon atoms,

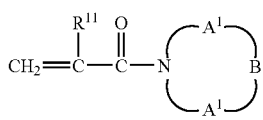
(II)

wherein $R^{11}$ has the same meaning as described above; $A^1$ and $A^2$, which may be identical or different, represents a group represented by formula: —(CH$_2$)m- (wherein m represents an integer from 2 to 6); and B represents —O— or a —CH$_2$— group,

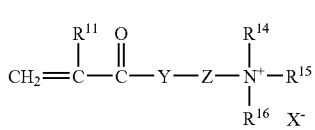
(III)

wherein $R^{11}$ has the same meaning as described above; $R^{14}$ and $R^{15}$, which may be identical or different, each represent an alkyl group or alkenyl group having 1 to 4 carbon atoms; $R^{16}$ represents a hydrogen atom or an alkyl group having 1 to 4 carbon atoms; Y represents —O—, —NH—, —CH$_2$— or —O—CH$_2$CH(OH)—; Z represents a straight-chained or branched alkylene group having 1 to 4 carbon atoms (provided that when Y is —CH$_2$—, the alkylene group has 0 to 3 carbon atoms); and X represents a conjugate base of an acid, a halogen atom or an alkyl sulfate group having 1 to 4 carbon atoms,

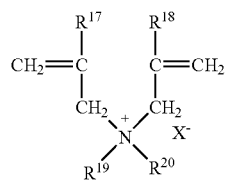
(IV)

wherein $R^{17}$ and $R^{18}$, which may be identical or different, each represent a hydrogen atom or a methyl group; $R^{19}$ and $R^{20}$, which may be identical or different, each represent a hydrogen atom or an alkyl group having 1 to 4 carbon atoms; and X has the same meaning as described above;

(b) a cationized cellulose derivative;
(c) a cationized guar gum derivative; and
(d) a diallyl quaternary ammonium salt polymer or a diallyl quaternary ammonium salt/acrylamide copolymer.

3. The skin or hair washing composition according to claim 2, wherein component (C) comprises (a).

4. The skin or hair washing composition according to claim 2, wherein component (C) comprises (b).

5. The skin or hair washing composition according to claim 2, wherein component (C) comprises (c).

6. The skin or hair washing composition according to claim 2, wherein component (C) comprises (d).

7. The skin or hair washing composition according to claim 1, wherein the component (B) comprises at least two surfactants, and one of the surfactants is sulfobetaine.

8. The skin or hair washing composition according to claim 1, wherein the weight ratio of the component (A) and the component (B), (A)/(B), is from 0.005 to 1.

9. The skin or hair washing composition according to claim 1, wherein n in the formula (1) of the component (A) is from 1.0 to 3.0.

10. The skin or hair washing composition according to claim 1, wherein the component (A) is contained in an amount of 0.1 to 20% by weight.

11. The skin or hair washing composition according to claim 1, wherein AO in the formula (1) of the component (A) is a propyleneoxy group having 3 carbon atoms.

12. The skin or hair washing composition according to claim 1, wherein a 20-fold dilution of the composition is at pH 4 to 10.

13. A method of washing skin or hair using a composition comprising the following components (A), (B) and (C), with the weight ratio of the component (A) and the component (C), (A)/(C), being from 0.5 to 30:

(A) a compound represented by formula (1):

$$R^1O\text{-}(AO)_n\text{—}R^2 \qquad (1)$$

wherein $R^1$ represents a straight-chained or branched alkyl group or alkenyl group having 8 carbon atoms; AO represents an alkyleneoxy group having 2 to 4 carbon atoms; n, the average number of added moles, represents a number from 0.5 to less than 4.0; and $R^2$ represents a hydrogen atom;

(B) a surfactant selected from the group consisting of a polyoxyethylene alkyl ether sulfate, a polyoxyethylene alkenyl ether sulfate, an alkyl sulfate, a higher fatty acid salt, a polyoxyalkylene alkyl ether acetate, an alkyl phosphate, a polyoxyalkylene alkyl ether phosphate, a polyoxyalkylene alkyl ether, an alkyl polyglucoside, a polyoxyalkylene C8-C20 fatty acid ester, a polyoxyalkylene sorbitan fatty acid ester, a polyoxyethylene hydrogenated castor oil, a fatty acid alkanolamide, a betaine-based surfactant, and an amine oxide surfactant;
(C) a cationic polymer.

14. A skin or hair washing composition, comprising the following components (A), (B) and (C):
(A) a compound represented by formula (1):

         (1)

wherein $R^1$ represents a straight-chained or branched alkyl group having 8 carbon atoms; AO represents an alkyleneoxy group having 2 to 4 carbon atoms; n, the average number of added moles, represents a number from 0.5 to less than 4.0; and $R^2$ represents a hydrogen atom;
(B) a surfactant other than the component (A);
(C) a cationic polymer,
wherein the weight ratio of the component (A) and the component (C), (A)/(C), is from 0.5 to 30.

15. The skin or hair washing composition according to claim 14, wherein AO is at least one of a propyleneoxy and an ethyleneoxy group.

16. The skin or hair washing composition according to claim 14, wherein n is 2.0 to 2.5.

17. The skin or hair washing composition according to claim 14, wherein $R^2$ is a hydrogen atom.

18. The skin or hair washing composition according to claim 14, wherein the component (A) is contained in an amount of 0.5 to 5% by weight.

19. A method of washing skin or hair using a composition comprising the following components (A), (B) and (C), with the weight ratio of the component (A) and the component (C), (A)/(C), being from 0.5 to 30:
(A) a compound represented by formula (1):

         (1)

wherein $R^1$ represents a straight-chained or branched alkyl group having 8 carbon atoms; AO represents an alkyleneoxy group having 2 to 4 carbon atoms; n, the average number of added moles, represents a number from 0.5 to less than 4.0; and $R^2$ represents a hydrogen atom;
(B) a surfactant other than the component (A);
(C) a cationic polymer.

* * * * *